United States Patent [19]
Ferone

[11] Patent Number: 5,820,828
[45] Date of Patent: Oct. 13, 1998

[54] MODULAR OZONE DISTRIBUTING SYSTEM

[76] Inventor: Daniel A. Ferone, 6038 Oakwood Ave., Cincinnati, Ohio 45224

[21] Appl. No.: 673,376

[22] Filed: Jun. 28, 1996

[51] Int. Cl.[6] ................................................. A62B 7/08
[52] U.S. Cl. ........................ 422/124; 422/112; 422/108; 422/114
[58] Field of Search ................................. 422/123, 124, 422/112, 114, 108

[56] References Cited

U.S. PATENT DOCUMENTS

| | | | |
|---|---|---|---|
| 1,056,789 | 3/1913 | Held | 422/186.07 |
| 2,345,798 | 4/1944 | Daily | 422/186.14 |
| 3,309,304 | 3/1967 | Caplan | 422/186.07 |
| 3,607,709 | 9/1971 | Rice | 422/186.15 |
| 3,838,290 | 9/1974 | Crooks | 422/186.07 |
| 3,967,131 | 6/1976 | Slipiec et al. | 422/186.18 |
| 4,545,960 | 10/1985 | Erz et al. | 422/186.12 |
| 4,606,892 | 8/1986 | Bachhofer et al. | 422/186.2 |
| 4,666,679 | 5/1987 | Masuda et al. | 422/186.2 |
| 4,726,824 | 2/1988 | Staten | 55/274 |
| 4,818,798 | 4/1989 | Bachhofer et al. | 422/186.2 |
| 4,892,713 | 1/1990 | Newman | 422/186.07 |
| 4,960,570 | 10/1990 | Mechtersheimer | 422/186.21 |
| 4,970,056 | 11/1990 | Wooten et al. | 422/186.07 |
| 5,009,858 | 4/1991 | Mechtersheimer | 422/186.19 |
| 5,087,418 | 2/1992 | Jacob | 422/23 |
| 5,137,697 | 8/1992 | Lathan et al. | 422/186.15 |
| 5,523,057 | 6/1996 | Mazzilli | 422/121 |
| 5,544,809 | 8/1996 | Keating et al. | 236/44 |

FOREIGN PATENT DOCUMENTS

| | | |
|---|---|---|
| 08042892 | 2/1996 | Japan . |
| 08098949 | 4/1996 | Japan . |

OTHER PUBLICATIONS

JAPIO abstract of JP08042892 (Nishimura Jiro), Feb. 16, 1996.
JAPIO abstract of JP08098949 (Ken et al.), Apr. 16, 1996.
JAPIO abstract of JP08066465 (Nakao Hidetoshi), Mar. 12, 1996.

*Primary Examiner*—Robert J. Warden
*Assistant Examiner*—Alex Noguerola
*Attorney, Agent, or Firm*—Wood, Herron & Evans, LLP

[57] ABSTRACT

A modular ozone distributing system for producing and distributing ozone to an air duct network of a building. The ozone distributing system includes an ozone generating unit for producing ozone from oxygen containing air and one or more ozone distributing units mounted to and in fluid communication with the air duct network connected to an HVAC system. Ozone produced by the ozone generating unit is delivered to each ozone distributing unit through a conduit. Each ozone distributing unit includes a high-speed blower which receives conditioned air from the air duct network and mixes it with the ozone delivered from the ozone generating unit for distribution into the air duct system. Control of ozone production by the ozone generating unit and distribution by the ozone distributing unit is provided by operation of the HVAC system.

24 Claims, 2 Drawing Sheets

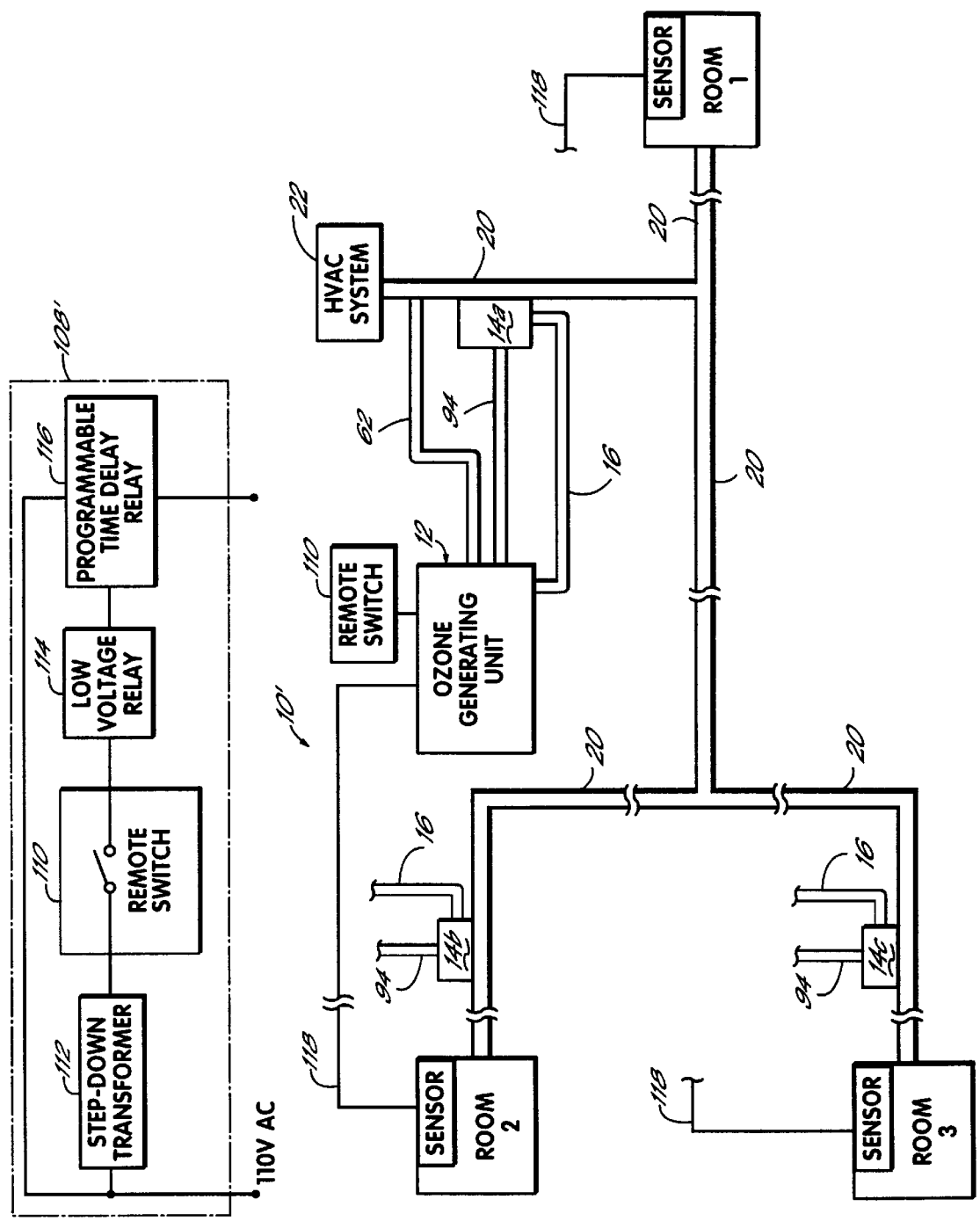

MODULAR OZONE DISTRIBUTING SYSTEM

FIELD OF THE INVENTION

The present invention relates generally to ozone generators and, more particularly, to systems for distributing ozone into air duct networks of buildings.

BACKGROUND OF THE INVENTION

Ozone is widely used throughout the world as a beneficial agent for destroying or eliminating bacteria and viruses, mold, fungi, and undesirable odors in household and commercial environments. To provide ozone in these and other environments, ozone generators have been developed to produce ozone from oxygen containing air passed through the ozone generator. Typically, ozone generators include one or more pairs of planar electrodes arranged in spaced apart and noncontacting relationship with dielectric plates disposed between the electrodes. In operation, the electrodes are energized by a high voltage AC source, typically having an output voltage exceeding 5,000 volts, to generate a corona or high energy electric field between the electrodes. Ozone is produced by passing oxygen containing air across the energized electrodes through air passages formed between the dielectric plates.

In the past, ozone generators have typically been constructed as self-contained units for producing ozone within an enclosed room or other relatively small and well-confined area. For this type of application, self-contained ozone generators are designed to provide a relatively uniform distribution of ozone within the intended area for cleaning and sterilizing the air. An example of such a self-contained ozone generator is disclosed in my U.S. Pat. No. 6,641,461, entitled "Ozone Generating Unit and Cell Therefor", which is incorporated herein by reference in its entirety. The ozone generator disclosed in my copending application is particularly adapted to be mounted above a suspended ceiling or on a wall through suitable means, and includes a diffuser vent for uniformly distributing ozone produced by the generator throughout the room or area.

However, where ozone is desired for cleaning and sterilizing air within several interconnected rooms, such as multiple rooms of a restaurant for example, a single ozone generator is less likely to produce uniform ozone distribution throughout all of the rooms for effective purification of the air. Moreover, where ozone is desired to clean and sterilize air within multiple isolated rooms of a building, such as an office building for example, the cost of providing self-contained ozone generators within each room or office may be substantial.

In those buildings which include a heating and ventilation (HVAC) system, it is known in the art to install all or part of the ozone generator directly in the air duct network for uniformly distributing ozone to ventilated rooms of the building. In one known design, the corona forming electrodes and dielectric plates are mounted within the air duct system, typically near and downstream of the HVAC system, while other components of the ozone generator are positioned outside of the duct network. The conditioned air from the HVAC system is forced across the electrodes and between the dielectric plates of the ozone generator to produce ozone which is then distributed downstream through the air duct network to ventilated rooms of the building.

However, to install an ozone generator of this design in the air duct system, the air duct must be opened and parts of the ozone generator mounted within the duct system which significantly increases the complexity and cost of installation. While an ozone generator of this design is capable of delivering ozone through the duct system to ventilated rooms of a building, the electrodes and dielectric plates of the ozone generator are subject to contamination by conditioned air from the HVAC system. Thus, when dust and other contaminants in the duct network eventually cover the electrodes and dielectric plates, the efficiency of the ozone generator is significantly reduced until the electrodes and dielectric plates are removed and cleaned. Moreover, with part of the ozone generator mounted within the air duct system, the flow of conditioned air from the HVAC system through the duct network is partially blocked, thereby resulting in a lower overall efficiency of the HVAC system.

To overcome the problems associated with installing all or part of the ozone generator directly in the air duct network, others have attempted to inject or pump ozone into the air duct network through distribution tubes or hoses attached to or mounted within the duct network. In this way, the ozone generator is positioned outside of the air duct network with only the distribution tube or hose interfacing directly with the duct network. However, with this type of system for distributing ozone, it has been found that conditioned air from the HVAC system does not mix well with ozone delivered to the air duct network through the distribution tubes or hoses. This improper mixing of the conditioned air and ozone in the air duct network generally results in a poor distribution of the ozone to ventilated rooms.

Moreover, another problem associated with known ozone distributing systems has been that the production of ozone is not controlled in any manner with operation of the HVAC system. That is, it is not uncommon for known ozone generators to produce or deliver ozone within the air duct network while the HVAC system is not operating to force conditioned air through the duct system. This creates a potentially dangerous situation where a high concentration of ozone is being produced or delivered within the air duct network without being safely mixed and distributed with conditioned air from the HVAC system. When this occurs, the level of ozone in one or more rooms ventilated by the air duct network may even become toxic.

SUMMARY OF THE INVENTION

Accordingly, a primary objective of the present invention is to provide a modular ozone distributing system which is easy to install and operate with an HVAC system for distributing ozone throughout an air duct network of a building.

Another objective of this invention is to provide an ozone distributing system which is reliable, easy to service and requires minimal periodic maintenance.

Yet another objective of this invention is to provide an ozone distributing system which distributes ozone efficiently through an air duct network to ventilated rooms of a building.

Still yet another objective of the present invention is to provide an ozone distributing system which is safely operable with an HVAC system to prevent dangerous levels of ozone from being produced and delivered into the air duct network of a building.

To these ends, a modular ozone distributing system is disclosed including an ozone generating unit for producing ozone from oxygen containing air and an ozone distributing unit fluidly connected to the ozone generating unit for distributing the ozone through an air duct network of a building. The ozone distributing unit is mounted to and in fluid communication with the air duct network and receives ozone produced by the ozone generating unit through a conduit. The ozone distributing unit is operable to receive conditioned air from the air duct network and to mix the conditioned air with ozone received from the ozone generating unit for distribution into the air duct system.

In a preferred embodiment of the present invention, the ozone distributing system includes a high-speed blower for mixing the conditioned air with the ozone received from the ozone generating unit for uniformly distributing the air and ozone mixture into the air duct network. The ozone generating unit and the ozone distributing unit are preferably operable to produce and distribute ozone only when the HVAC system connected to the air duct network is operating to circulate conditioned air through the duct system.

The objectives and features of the present invention will come readily apparent when the following Detailed Description is taken in conjunction with the accompanying drawings in which:

BRIEF DESCRIPTION OF THE DRAWINGS

FIG. 1A is a schematic diagram of a remote switch for use with the ozone distributing system shown in FIG. 1; and FIG. 2 is a diagrammatic view of an alternative embodiment of the ozone distributing system shown in FIG. 1.

DETAILED DESCRIPTION OF THE INVENTION

Figure 1:
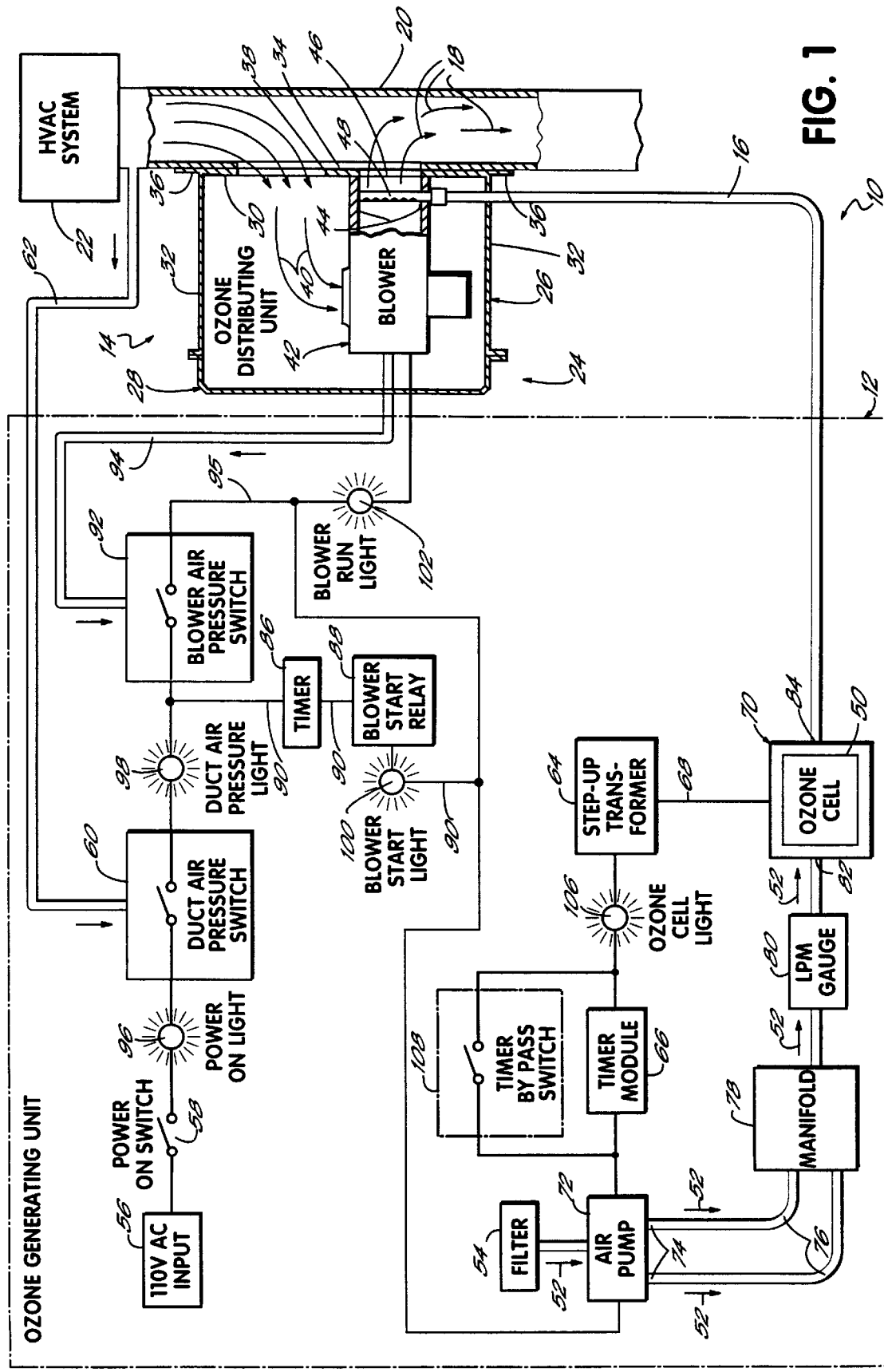
FIG. 1 is a schematic diagram of an ozone distributing system in accordance with a preferred embodiment of the present invention.

With reference to the drawings, and to FIG. 1 in particular, an ozone distributing system 10 in accordance with the principles of the present invention is shown. Ozone distributing system 10 includes a self-contained ozone generating unit 12 for producing ozone from oxygen containing air and an ozone distributing unit 14 fluidly connected to the ozone generating unit through conduit 16. In accordance with the present invention, the ozone distributing unit 14 is particularly adapted to receive ozone produced by the ozone generating unit 12 through conduit 16 and to distribute the ozone, shown diagrammatically by arrows 18, into an air duct network 20 of a building as will be described in more detail below.

As shown in FIG. 1, the ozone distributing unit 14 is mounted externally to and in fluid communication with the air duct network 20, which is itself connected to a standard HVAC system 22. Preferably, the ozone distributing unit 14 includes a generally rectangular housing 24 having a base 26 and a top 28 made of fiberglass or other suitable ozone resistant material. The base 26 includes a bottom 30 which is preferably integrally molded with a pair of end walls 32 and a pair of side walls (not shown). The top 28 is hinged to the base 26 along one of the side walls and is further sealingly engageable with an upper peripheral edge of the base through a gasket (not shown) disposed about a peripheral edge of the top. A pair of latches (not shown) is provided to secure the top 28 in a closed position with the base 26 as is shown in FIG. 1.

To install the ozone distributing unit 14 to the air duct network 20 of the HVAC system 22, which may comprise a standard 24" or 48" HVAC duct system for example, an opening 34 is provided in the duct network preferably near and downstream of the HVAC system. The base 26 of the ozone distributing unit 14 is secured to the air duct network 20 through fasteners (not shown) which extend through integral bottom flanges 36 and into one side of the air duct. The bottom 30 of the ozone distributing unit 14 includes an air inlet 38 overlying the opening 34 for receiving conditioned air, shown diagrammatically by arrows 40, from the HVAC system 22. A high-speed blower 42, preferably operating between about 1800 and about 3400 RPM, is mounted in the ozone distributing unit 14 for receiving the conditioned air 40 through air inlet 38 and mixing it with ozone received from the ozone generating unit 12 through conduit 16. The blower 42 preferably includes an air discharge channel 44 extending to an ozone outlet 46 in the bottom 30 which also overlies the opening 34. An ozone distributor 48 is fluidly connected to the conduit 16 and mounted within the air discharge channel 44 for distributing ozone produced by the ozone generating unit 12. During a preferred operation of the ozone distributing unit 14, ozone is communicated from the ozone generator unit 12 to the ozone distributor 48 through conduit 16. The blower 42 receives conditioned air 40 from the air duct network 20 through air inlet 38, and mixes it with the ozone distributed by the ozone distributor 48 for distribution into the air duct network through ozone outlet 46, as shown diagrammatically by arrows 18.

The ozone generating unit 12 of the present invention is particularly adapted to produce ozone from oxygen containing air and to communicate the ozone to the ozone distributing unit 14 through the conduit 16. As disclosed in my copending application to which the reader is referred, the ozone generating unit 12 is self-contained in a housing and includes one or more ozone generator cells 50 for producing ozone from oxygen containing air, shown diagrammatically by arrows 52 in FIG. 1, received through air filter 54. A preferred ozone generator cell 50 for use in the ozone generating unit 12 is commercially available from Rainbows, Inc. of Cincinnati, Ohio, the construction and operation of which are disclosed in my U.S. Pat. No. 5,641,461, entitled "Ozone Generating Unit and Cell Therefor", which is incorporated herein by reference in its entirety. Ozone produced by the ozone generator cell 50 is communicated to the ozone distributing unit 14 through conduit 16 for distribution into the air duct network 20 as will be described in more detail below.

With further reference to FIG. 1, the ozone generating unit 12 is energized by a standard 110 VAC input or line 56 extending into the housing (not shown) of the ozone generating unit and controlled by a power on switch 58. A duct air pressure switch 60 is provided to connect and disconnect the 110 VAC input 56 from various components associated with the ozone generator cell 50 in response to on and off operation of the HVAC system 22. The duct air pressure switch 60 is fluidly connected to the air duct network 20 through a conduit 62 which extends between the ozone generating unit 12 and the air duct network. A pitot tube (not shown) is mounted in the air duct network 20 and connected to the conduit 62. In this way, when the HVAC system 22 is operating to circulate conditioned air 40 in the air duct network 20, thereby producing between about 0.1" and about 1.0" of positive pressure in conduit 62, the duct air pressure switch 60 will close to energize the ozone generating unit 12 for the production of ozone as will be described in more detail below. When the HVAC system 22 is not operating, the duct air pressure switch 60 will open to disconnect the ozone generating unit 12 from the 110 VAC line 56.

With further reference to FIG. 1, a high voltage step-up transformer 64 is provided having its primary energized by the 110 VAC line 56 through a timer module 66. The high voltage step-up transformer 64 has its secondary coupled through electrical leads 68 to the ozone generator cell 50 which is mounted within an enclosure 70. The step-up transformer 64 has a preferred output voltage in a range between about 7,000 and 8,000 volts.

The ozone generating unit 12 further includes a diaphragm air pump 72 which is energized by the 110 VAC line 56 and receives oxygen containing air 52 through the air filter 54. The air pump 72 includes a pair of air exhaust ports 74 for discharging the filtered oxygen containing air 52 through a pair of flexible conduits 76 to a manifold 78. The manifold 78 is preferably fluidly connected to an LPM (liters-per-minute) gauge 80, which is itself fluidly connected to an air intake port 82 formed in the enclosure 70 for delivering the oxygen containing air 52 to the ozone generator cell 50 within the enclosure. Preferably, the air pump 72 has an output volume of at least 10 liters/min. to sufficiently cool the ozone generator cell 50 during its operation as will be described in more detail below.

The enclosure 70 further includes an ozone exhaust port 84 for discharging ozone produced by the ozone generator cell 50 through the conduit 16. As described above, the conduit 16 fluidly connects the ozone exhaust port 84 of the enclosure 70 to the ozone distributor 48 for discharging ozone produced by the ozone generator cell 50. Preferably, the ozone distributor 48 is made of a perforated stainless steel tube which is resistant to pitting or other deterioration by ozone produced by the ozone generator cell 50. In an alternative embodiment, the ozone distributor 48 is made of a perforated fluoronated polyethylene tubing (preferably Chemfluor) which is also resistant to ozone deterioration.

With further reference to FIG. 1, when the duct air pressure switch 60 is closed, the blower 42 is initially energized by the 110 VAC line 56 through a timer 86 and blower start relay 88 connected in an electrical path 90 as will be described in more detail below. The blower 42 is also coupled to the 110 VAC line 56 through a blower air pressure switch 92 which is fluidly connected to the blower through a conduit 94 which extends between the ozone generating unit 12 and the blower. A pitot tube (not shown) is preferably mounted in the air discharge channel 44 of blower 42, and connected to the conduit 94. In this way, when the blower 42 is operating to mix the conditioned air 40 with the ozone for distribution into the air duct network 20, as represented by arrows 18, a positive pressure is created in the conduit 94 to close the blower air pressure switch 92. Thus, when the 110 VAC input 56 has been disconnected from the blower 42 through the timer 86 and blower start relay 88, i.e., the electrical path 90, the blower is energized by the 110 VAC input through an electrical path 95 created by the blower air pressure switch 92.

In accordance with the present invention, the duct air pressure switch 60 and blower air pressure switch 92 provide a safeguard in the operation of ozone distributing system 10. The ozone generating unit 12 will only produce ozone when the duct air pressure switch 60 is closed, thereby indicating that the HVAC system 22 is operating to circulate conditioned air 40 in the air duct network 20 at a predetermined pressure/volume, and the blower air pressure switch 92 is closed, thereby indicating that the blower 42 is operating to distribute the mixed air and ozone combination 18 into the air duct network. Thus, in the case of dirty filters in the HVAC system 22, for example, the duct air pressure switch 60 will open as a result of the reduced air pressure/volume to shut down the ozone generating unit 12. If either pressure switch 60 or 92 opens, various components associated with the ozone generator cell 50 will not operate to prevent the potentially harmful production of ozone as will be described in more detail below. Moreover, with this arrangement of components, it will be appreciated that the ozone generating unit 12 will cycle with the on/off operation of the HVAC system 22.

In a preferred operation of the ozone distributing system 10 shown in FIG. 1, the 110 VAC input line 56 is plugged into a standard electrical wall outlet to energize the ozone generating unit 12. Upon actuation of the power switch 58, a power on light 96 mounted on the housing of the ozone generating unit 12 illuminates to indicate that the ozone generating unit is in a "power on" mode. In the "power on" mode, the ozone generating unit 12 is operable to produce ozone when both the HVAC system 22 and blower 42 are operating to close duct air pressure switch 60 and blower air pressure switch 92, respectively. When the HVAC system 22 is operating to close the duct air pressure switch 60 through positive pressure created in conduit 62, a duct air pressure light 98 mounted on the housing of the ozone generating unit 12 illuminates to indicate that the HVAC system 22 is operating and the duct air pressure switch 60 is closed. Upon closure of duct air pressure switch 60, timer 86 initiates to energize blower start relay 88 for a predetermined duration of time, such as five (5) seconds for example, to energize the blower 42 and components associated with the ozone generator cell 50 through electrical path 90. A blower start light 100 mounted on the housing of the ozone generating unit 12 illuminates during this predetermined duration of time to indicate that the blower 42 is energized. At the same time, a blower run light 102 mounted on the housing of the ozone generating unit 12 also illuminates to indicate that the blower 42 is energized. As the blower 42 is energized during this predetermined duration of time through electrical path 90, the blower air pressure switch 92 will close as a result of the positive pressure created in conduit 94 by operation of the blower. After the timer 86 times out, thereby disconnecting the 110 VAC line 56 through the electrical path 90, the blower 42 and components associated with the ozone generator cell 50 will remain energized through electrical path 95 until either the duct air pressure switch 60 or blower air pressure switch 92 opens to disconnect the 110 VAC line 56.

With either the electrical path 90 or 95 is energized, the 110 VAC input line 56 is coupled to the air pump 72 and the timer module 66. When the air pump 72 is energized, it receives the oxygen containing air 52 through the air filter 54. The air pump 72 communicates the filtered oxygen containing air 52 through the air exhaust ports 74, conduits 76, manifold 78, and LPM gauge 80 to the air intake port 82 of the ozone generator cell enclosure 70.

When either the electrical path 90 or 95 is energized, the timer module 66 is energized to selectively operate or cycle the step-up transformer 64 between "on" and "off" states, e.g., 10 seconds "on" and 10 seconds "off". Preferably, the timer module 66 is selectively settable through fixed or variable resistors to define the duration of the "on" and "off" cycles of the step-up transformer 64. When the step-up transformer 64 is in an "on state", the electrodes of the ozone generator cell 50 are energized by the electrical leads 68 to produce ozone from the oxygen containing air 52 received through the air intake port 82. An ozone cell light 106 mounted on the housing of the ozone generating unit 12 illuminates to indicate that the ozone generator cell 50 is energized to produce ozone.

The ozone produced by the ozone generator cell 50 is discharged from the enclosure 70 through the ozone exhaust port 84 and conduit 16. As described in detail above, the conduit 16 is fluidly connected to the ozone distributor 48 mounted within the air discharge channel 44 of the blower 42 for discharging ozone produced by the ozone generator cell 50. The blower 42 drives the conditioned air 52 to mix with the ozone discharged from the ozone distributor 48 and distributes the air and ozone mixture, shown diagrammatically by arrows 18, into the air duct network 20.

In one embodiment as shown in FIG. 1, a manual timer by-pass switch 108 is provided to by-pass operation of the timer module 66. When the timer by-pass switch 108 is closed, the step-up transformer 64, and thus the ozone generator cell 50, is energized independently of the state of the timer module 66 until the timer by-pass switch is opened. Use of the timer by-pass switch 108 is desirable when continuous, rather than cyclic, operation of the ozone generating cell 50 is desired during operation of the HVAC system 22.

In an alternative embodiment shown in FIG. 1A, the timer by-pass switch 108 of FIG. 1 is replaced with the remote switch circuitry 108' of FIG. 1A. In this embodiment, the 110 VAC line 56 is coupled to a remote switch 110, e.g. a 24 V switch, through a step-down transformer 112. The remote switch 110 is coupled to a low voltage relay 114 which in turn is coupled to a programmable time delay relay 116 for switching the 110 VAC line to the step-up transformer 64. When the remote switch 110 is closed, the timer module 66 is by-passed (overridden) and the programmable time delay relay 116 closes to energize, through step-up transformer 64, the ozone generator cell 50 a predetermined duration of time, e.g. 4 hours, independently of the state of the timer module 66.

The remote switch circuitry 108' of FIG. 1A is particularly useful in restaurant and bar environments, for example, where continuous ozone production may be required only during peak hours to remove heavy smoke from the air. During off-peak periods, the timer module 66 controls ozone production as described in detail above. While not shown, those skilled in the art will appreciate that a remote ozone cell light may be provided at the remote switch 110 to indicate that the ozone generator cell 50 is energized and operating through the programmable time delay relay 116.

In another embodiment, the remote switch circuitry 108' of FIG. 1A is placed in parallel with the timer by-pass switch 108 of FIG. 1. In this embodiment, the ozone generator cell 50 is energized by the timer module 66 when the timer by-pass switch 108 of FIG. 1 and the remote switch 110 of FIG. 1A are open. If the remote switch 110 is closed and the timer by-pass switch 108 is open, the ozone generator cell 50 is energized by the programmable time delay relay 116 until the relay opens after the extended preset time period. If the timer by-pass switch 108 is closed, the ozone generator cell 50 is energized, independently of the states of the timer module 66 and programmable time delay relay 116, until the timer by-pass switch 108 is opened. In this way, the ozone generating unit 12 is operable in three modes of operation, i.e., cyclic, continuous, and cyclic with remote switch override, to accommodate for different ozone production needs of a user during operation of the HVAC system 22.

As shown in the alternative embodiment of FIG. 2, the present invention contemplates an ozone distributing system 10' having multiple ozone distributing units 14a, 14b and 14c mounted to and in fluid communication with an air duct network 20 at spaced apart locations for distributing ozone to remotely ventilated rooms of a building. In this embodiment, a single ozone generating unit 12 is provided to operate with the multiple ozone distributing units 14a, 14b and 14c in generally the same manner as described above. However, in this embodiment, the ozone generating unit 12 preferably has a separate blower air pressure switch 92, conduit 94, air pump 72, step-up transformer 64, ozone generator cell 50, and conduit 16 for operating with each of the ozone distributing units 14a, 14b and 14c. In this way, the concentration of ozone within the air duct network 20 may be maintained at a relatively constant level throughout the duct network for distribution to the remotely ventilated rooms of the building.

In another contemplated embodiment as shown in FIG. 2, one or more of the ventilated rooms includes a conventional motion, occupancy or volatile organic compound (VOC) sensor with the ability to detect smoke particles, for example, to control distribution of ozone from the ozone generating unit 12 to each particular room. Thus, when the sensors detect certain conditions within the rooms, e.g., motion, a certain number of persons, or a level of air pollution above a preset threshold, the sensors generate appropriate electrical signals indicative of the conditions though conductors 118 which are then received by the ozone generating unit 12. Thus, the production of ozone by the ozone generating unit 12 for each of the ozone distributing units 14a, 14b, and 14c may be separately controlled by each sensor within a ventilated room.

In one embodiment, each sensor may be operable to send only one type of signal, e.g. a signal of a predetermined voltage or frequency, which is indicative of the condition within the room. In another embodiment, each sensor may be operable to produce varying types of signals, e.g. signals of varying voltages or frequencies, to indicate different levels of conditions within the room. In the first embodiment, the ozone generating unit 12 is operable to produce ozone for a predetermined duration of time in response to the one type of sensor signal. In the second embodiment, the ozone generating apparatus is operable to produce ozone for varying durations of time in response to the varying sensor signals. In this way, the sensors may produce signals of four (4) different levels to produce ozone in 25%, 50% 75% and 100% increments of a predetermined duration, for example. Thus, it may be desirable to have the ozone generating unit 12 produce ozone for a greater duration of time in the event a higher level of pollution is detected within a room, with automatic reduction of ozone production when the pollution level decreases.

As will be appreciated from the detailed description above, the ozone distributing system 10 of the present invention is particularly adapted for distributing ozone throughout an air duct network of a building. The design of the ozone distributing system 10 makes it readily useable with an HVAC system for efficient distribution of ozone to ventilated rooms of a building. By delivering ozone to the ozone distributing unit 14 and having the high-speed blower mix the conditioned air with the ozone at the air duct network 20, a uniform distribution of ozone throughout the air duct network is achieved. The ozone distributing unit 14 is easily mounted on the air duct network 20 with virtually no modification to the HVAC duct system. The modular construction of the ozone distributing system 10 also makes it easy to service and maintain. In the event the ozone generating unit 12 or ozone distributing unit 14 should fail, only that part of the ozone distributing system 10 needs to be replaced, thereby reducing any downtime of the ozone distributing system for service. Moreover, the ozone distributing system 10 is safely operable with the HVAC system to prevent dangerous levels of ozone from being produced and delivered in the air duct network.

From the above disclosure of the general principles of the present invention and the preceding detailed description of the preferred embodiments, those skilled in the art will readily comprehend the various modifications to which the present invention is susceptible. Therefore, Applicant desires to be limited only by the scope of the claims and equivalents thereof.

What is claimed is:

1. An apparatus for distributing ozone to an air duct network of a building, said air duct being fluidly connected to a source of conditioned air, comprising:
an ozone distributing unit mounted externally to and in fluid communication with said air duct network; and
an ozone generating unit adapted to produce ozone from oxygen containing air and deliver said ozone to said ozone distributing unit independently of said air duct network,
said ozone distributing unit adapted to receive conditioned air from said air duct network and mix said conditioned air with said ozone for distributing a mixture of said conditioned air and ozone into said air duct network.

2. The ozone distributing apparatus of claim 1 further comprising a forced air device mounted within said ozone distributing unit, said forced air device mixing said conditioned air with said ozone for driving a mixture of said conditioned air and ozone into said air duct network.

3. The ozone distributing apparatus of claim 1 wherein said ozone generating unit includes a timer for selectively operating components of said ozone generating unit between "on" and "off" states, said ozone generating unit producing ozone during said "on" state.

4. The ozone distributing apparatus of claim 3 wherein said timer is selectively settable to define a duration for at least one of said "on" and "off" states.

5. The ozone distributing apparatus of claim 3 further including a remote switch coupled to said ozone generating unit and operable to by-pass said timer when said remote switch is closed, components of said ozone generating unit being operable in said "on" state for a duration of time when said remote switch is closed, said ozone generating unit producing ozone during said "on" state.

6. The ozone distribution apparatus of claim 1 further comprising at least one element responsive to a selected air pressure in said air duct network, said element operatively controlling components of said ozone generating unit in an "on" state responsive to said selected air pressure in said air duct network, said ozone generating unit producing ozone during said "on" state.

7. An apparatus for distributing ozone to an air duct network of a building having a plurality of enclosed rooms, said air duct being fluidly connected to a source of conditioned air, comprising:
an ozone generating unit adapted to produce ozone from oxygen containing air;
at least two ozone distributing units mounted externally to and in fluid communication with said air duct network at spaced apart locations; and
a conduit extending between said ozone generating unit and each of said ozone distributing units, each of said conduits adapted to deliver ozone produced by said ozone generating unit to each of said ozone distributing units independently of said air duct network,
each of said ozone distributing units adapted to receive conditioned air from said air duct network and mix said conditioned air with said ozone for distribution into said air duct network at said spaced apart locations.

8. The ozone distributing apparatus of claim 7 further comprising a forced air device mounted within each of said ozone distributing units, each of said forced air devices driving said conditioned air in mixed combination with said ozone for distribution into said air duct network at said spaced apart locations.

9. The ozone distributing apparatus of claim 7 wherein said ozone generating unit includes a timer for selectively operating components of said ozone generating unit between "on" and "off" states, said ozone generating unit producing ozone during said "on" state.

10. The ozone distributing apparatus of claim 9 wherein said timer is selectively settable to define a duration for at least one of said "on" and "off" states.

11. The ozone distributing apparatus of claim 9 further including a remote switch coupled to said ozone generating unit and operable to by-pass said timer when said remote switch is closed, components of said ozone generating unit being operable in said "on" state for a duration of time when said remote switch is closed, said ozone generating unit producing ozone during said "on" state.

12. The ozone distribution apparatus of claim 7 further comprising at least one element responsive to a selected air pressure in said air duct network, said element operatively controlling components of said ozone generating unit in an "on" state responsive to said selected air pressure in said air duct network, said ozone generating unit producing ozone during said "on" state.

13. The ozone distributing apparatus of claim 7 wherein at least one of said rooms includes a sensor operable to produce an electrical signal responsive to a condition within said room, said ozone generating unit receiving said electrical signal from said sensor indicative of said condition within said room and to producing ozone for a duration of time in response to said electrical signal.

14. The ozone distributing apparatus of claim 13 wherein said sensor is operable to generate a plurality of different electrical signals responsive to a plurality of different conditions within said room, said ozone generating unit receiving said plurality of electric signals from said sensor indicative of said plurality of different conditions within said room and producing ozone for varying durations of time in response to said plurality of electrical signals.

15. The ozone distributing apparatus of claim 13 wherein said sensor comprises an air pollutant sensor.

16. The ozone distributing apparatus of claim 13 wherein said sensor comprises a motion sensor.

17. The ozone distributing apparatus of claim 13 wherein said sensor comprises an ozone sensor.

18. An ozone distributing unit for use in combination with an ozone generating unit in a system for distributing ozone to an air duct network of a building, said air duct being fluidly connected to a source of conditioned air, comprising:
a housing mounted to an external surface of said air duct network and in fluid communication therewith adapted to receive conditioned air from said air duct network;
an ozone distributor mounted within said housing and in fluid communication with an ozone generating unit independently of said air duct network for discharging ozone produced by said ozone generating unit; and
a forced air device mounted within said housing adapted to mix said conditioned air with said ozone and distribute the mixture into said air duct network.

19. The ozone distributing unit of claim 18 wherein said forced air device comprises a blower.

20. An ozone distributing unit for use in combination with an ozone generating unit in a system for distributing ozone to an air duct network of a building, said air duct being fluidly connected to a source of conditioned air comprising:
- a housing mounted to an external surface of said air duct network and in fluid communication therewith;
- an ozone distributor mounted within said housing and in fluid communication with an ozone generating unit independently of said air duct network for discharging ozone produced by said ozone generating unit,
- said housing having an air inlet adapted to receive conditioned air from said air duct network and an ozone outlet adapted to distribute said conditioned air and ozone into said air duct network; and
- a forced air device mounted within said housing adapted to mix said conditioned air with said ozone for distribution into said air duct network through said ozone outlet.

21. The ozone distributing unit of claim 20 wherein said forced air device comprises a blower.

22. The ozone distributing unit of claim 21 wherein said blower includes an air discharge channel extending to said ozone outlet, said ozone distributor being mounted within said air discharge channel.

23. The ozone distributing unit of claim 20 wherein said ozone distributor comprises a perforated stainless steel tube.

24. The ozone distributing unit of claim 20 wherein said ozone distributor comprises a perforated fluoronated polyethylene tube.

* * * * *

UNITED STATES PATENT AND TRADEMARK OFFICE
CERTIFICATE OF CORRECTION

PATENT NO. : 5,820,828
DATED : October 13, 1998
INVENTOR(S) : Daniel A. Ferone

It is certified that error appears in the above-identified patent and that said Letters Patent is hereby corrected as shown below:

Column 1, line 34, please delete "6,641,461" and replace with --5,641,461--.

Signed and Sealed this

Thirtieth Day of March, 1999

Attest:

Q. TODD DICKINSON

Attesting Officer

Acting Commissioner of Patents and Trademarks